(12) United States Patent
Chan et al.

(10) Patent No.: US 9,994,903 B2
(45) Date of Patent: Jun. 12, 2018

(54) TRANSCRIPTOMIC INDEX FOR CHARACTERIZING THE CELLULAR REPAIR RESPONSE AFTER SOFT TISSUE INJURY IN DIARTHRODIAL JOINTS

(71) Applicant: RUSH UNIVERSITY MEDICAL CENTER, Chicago, IL (US)

(72) Inventors: Deva Chan, Chicago, IL (US); Jun Li, Chicago, IL (US); Anna H. K. Plaas, Chicago, IL (US); John D. Sandy, Chicago, IL (US); Vincent Wang, Chicago, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 0 days. days.

(21) Appl. No.: 14/916,817

(22) PCT Filed: Sep. 8, 2014

(86) PCT No.: PCT/US2014/054550
§ 371 (c)(1),
(2) Date: Mar. 4, 2016

(87) PCT Pub. No.: WO2015/038474
PCT Pub. Date: Mar. 19, 2015

(65) Prior Publication Data
US 2016/0215342 A1 Jul. 28, 2016

Related U.S. Application Data

(60) Provisional application No. 61/877,011, filed on Sep. 12, 2013.

(51) Int. Cl.
*A01N 43/04* (2006.01)
*C12Q 1/68* (2018.01)

(52) U.S. Cl.
CPC ..... *C12Q 1/6883* (2013.01); *C12Q 2600/106* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2003/0032098 A1 | 2/2003 | Young et al. |
| 2004/0037841 A1 | 2/2004 | Liew et al. |
| 2009/0068656 A1 | 3/2009 | Beier et al. |
| 2010/0129798 A1 | 5/2010 | Abramson et al. |
| 2011/0020809 A1 | 1/2011 | Liew et al. |
| 2013/0178442 A1 | 7/2013 | Scanzello et al. |

FOREIGN PATENT DOCUMENTS

WO   WO2012/061821   5/2012

OTHER PUBLICATIONS

Supplementary European Search Report dated Apr. 7, 2017, 13 pgs.
TC TM Van Der Pouw Kraan et al: 1-15, "Discovery of distinctive gene expression profiles in rheumatoid synovium using cDNA microarray technology: evidence for the existence of multiple pathways of tissue destruction and repair", Genes and Immunity, vol. 4, No. 3, Apr. 1, 2003 (Apr. 1, 2003), pp. 187-196.
Daghestani, et al., "Soluble Macrophage Biomarkers Indicate Inflammatory Phenotypes in Patients With Knee Osteoarthritis", Arthritis Rheumatology vol. 67, No. 4, Apr. 2015, 10 pgs.
Geurts, et al., "Elevated Marrow Inflammatory Cells and Osteoclasts in Subchondral Osteosclerosis in Human Knee Osteoarthritis", Journal of Orthopaedic Research, Feb. 2016, 8 pgs.
Chan, et al., "Deficiency of hyaluronan synthase 1 (Has1) results in chronic joint inflammation and widespread intra-articular fibrosis in a murine model of knee joint cartilage damage", Osteoarthritis and Cartilage, 2015, 13 pgs.
Yu, et al., "MyD88-dependent interplay between myeloid and endothelial cells in the initiation and progression of obesity-associated inflammatory diseases", Journal of Experimental Medicine, 2014, 22 pgs.
Weisser, et al., "Generation and Characterization of Murine Alternatively Activated Macrophages", Methods in Molecular Biology, vol. 946, 2013, 15 pgs.
Hamilton, et al., "Myleloid colony-stimulating factors as regulators of macrophage polarization", Frontiers in Immunology, Nov. 2014, vol. 5, 15 pgs.
He, et al., "GATA3 Transcription Factor Abrogates Smad4 Transcription Factor-mediated Fascin Overexpression, Invadopodium Formation, and Breast Cancer Cell Invation", Journal of Boilogical Chemistry, vol. 288, No. 52, Dec. 2013, 14 pgs.
Chan et al., "Can the presence of subchondral cyst—an indicatory of subchondral bone disturbance, be used for subtyping knee osteoarthritis?", Abstracts/Osteoarthritis and Cartilage 23 (2015), 2 pgs.
Chan et al., "Spontaneous development of sclerotic changes of subchondral bone and cartilage degradation in endothelin-1 overexpression transgenic mice upon high fat/high cholesterol diet", Abstracts/Osteoarthritis and Cartilage 23 (2015), 2 pgs.
International Search Report for PCT/US2014/054550 dated Dec. 12, 2014 (10 pgs. including Search History).
Written Opinion for PCT/US2014/054550 dated Dec. 12, 2014 (6 pgs.).

(Continued)

*Primary Examiner* — Ekaterina Poliakova-Georgantas
(74) *Attorney, Agent, or Firm* — Brinks Gilson & Lione

(57) ABSTRACT

One aspect of the Invention provides methods for classifying the quality of a repair response after injury to a joint of a subject. In one embodiment, the method includes providing a tissue sample from the injured region of the joint and determining expression levels in the sample of a plurality of genes, including at least those genes listed in Table 1, Table 2 and Table 3, Another aspect of the Invention provides methods of treating a human or veterinary subject having an injury to a joint based on the classification of the quality of the repair response.

11 Claims, 3 Drawing Sheets

(56) References Cited

OTHER PUBLICATIONS

Matsen, III, Frederick A.; Joints. UW Medicine Orthopaedics and Sports Medicine (online), (retrieved on Nov. 6, 2014), 8 pgs.
Examination Report for EP14844103.3 dated Apr. 30, 2018, 7 pgs.

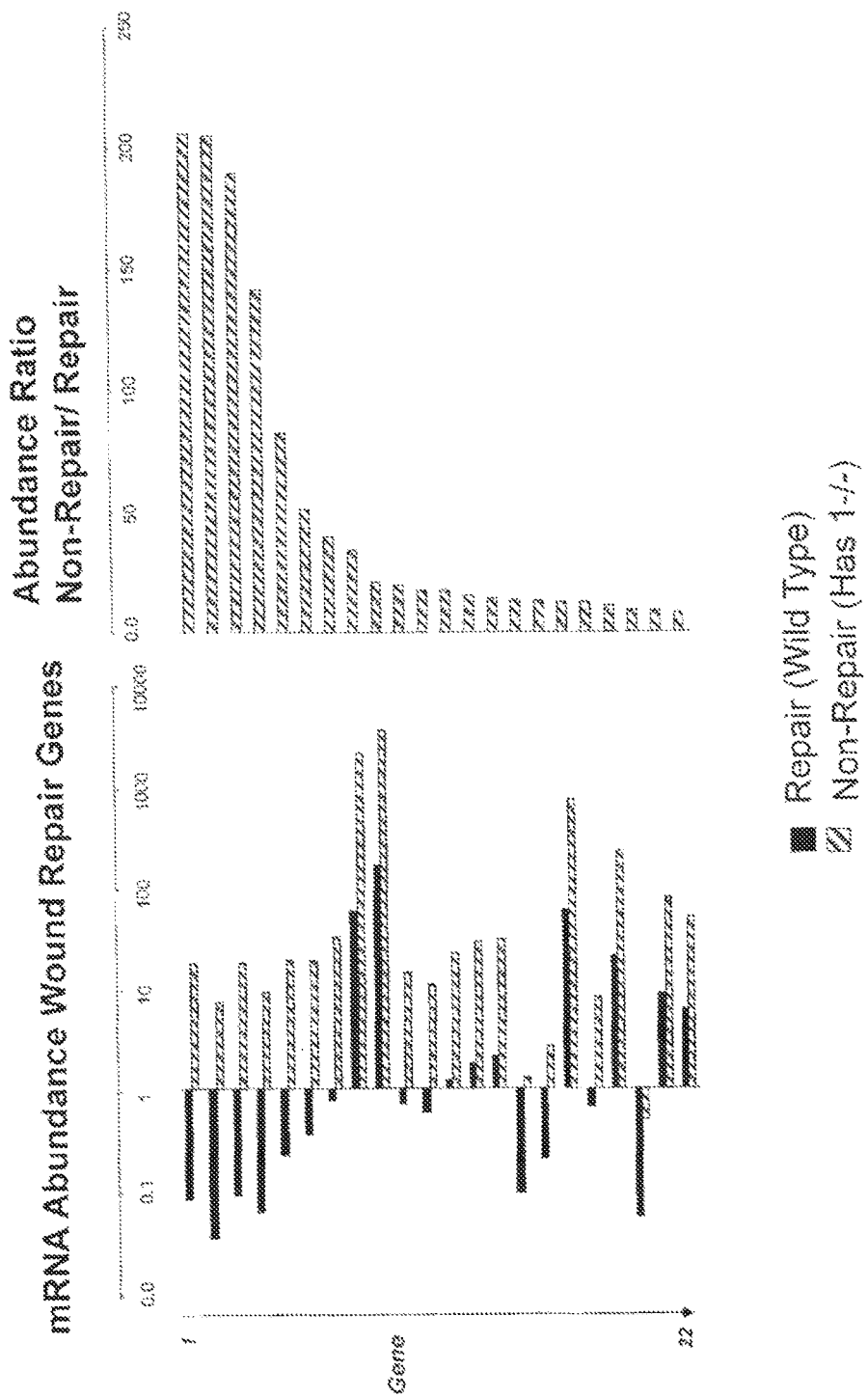

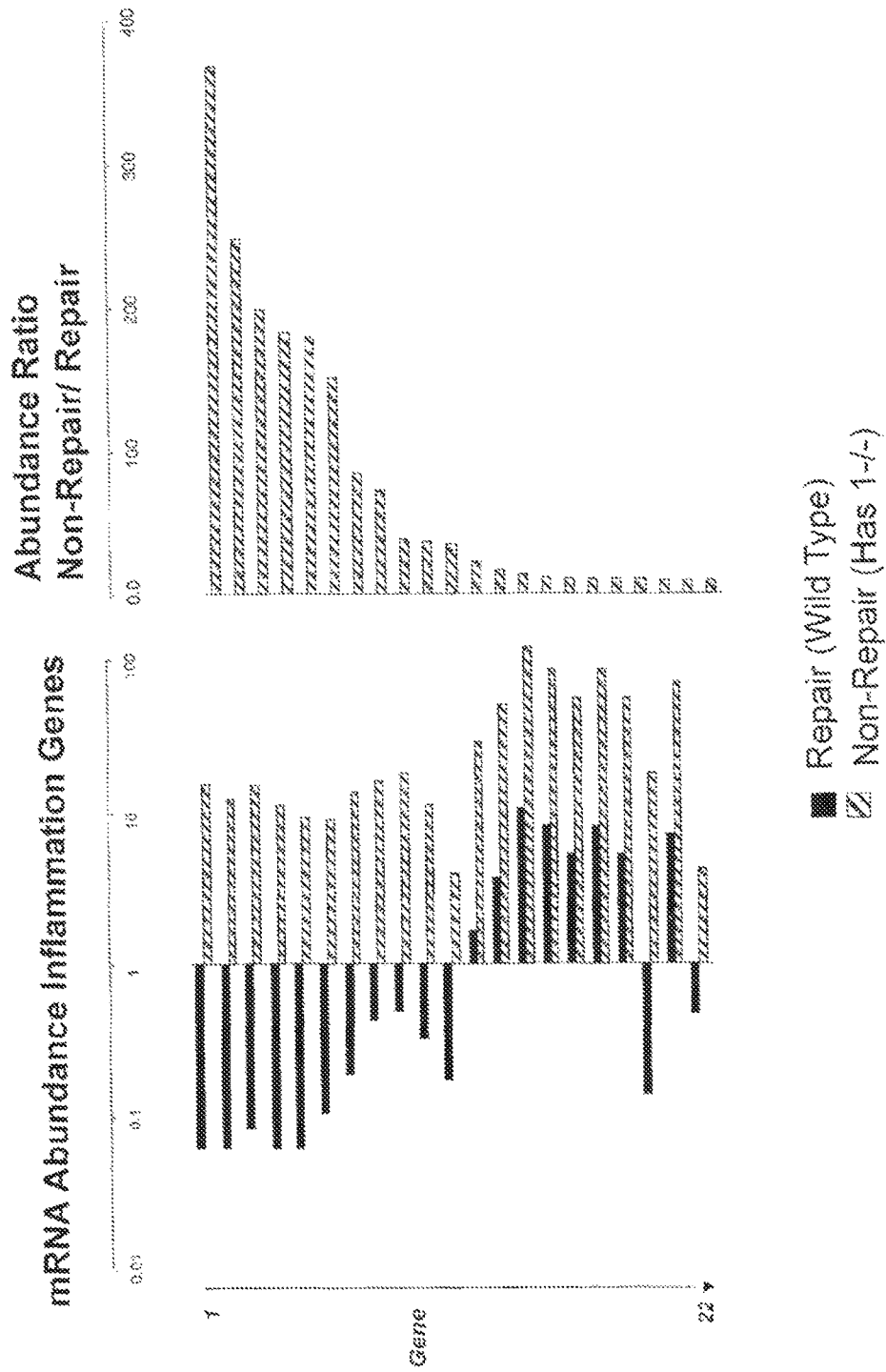

TRANSCRIPTOMIC INDEX FOR CHARACTERIZING THE CELLULAR REPAIR RESPONSE AFTER SOFT TISSUE INJURY IN DIARTHRODIAL JOINTS

RELATED APPLICATIONS

This application is a National Stage of PCT/US2014/054550, filed Sep. 8, 2015, which claims the benefit of the filing date of U.S. Provisional Patent Application No. 61/877,011, filed Sep. 12, 2013, the contents of which is hereby incorporated by reference.

STATEMENT AS TO RIGHTS TO INVENTIONS MADE UNDER FEDERALLY SPONSORED RESEARCH AND DEVELOPMENT

This invention was made with Government support of Grant No. R01-AR057066 awarded by the National Institutes of Health. The Federal Government has certain rights in this invention.

TECHNICAL FIELD

The present invention generally relates to methods for determining the quality of recovery from joint injury and to methods of treating joint injury based on such determinations.

BACKGROUND

Increasing degrees of force applied to joints result in joint injury. Such joint injury is frequently seen as a result of trauma, for example chondral lesions are often seen in athletes, and are typically associated with acute inflammation. The treatment of joint injuries (such as ligamentous rupture or meniscal tearing) and rehabilitation of the patient after such injuries involves a number of components. Immediate care after the injury typically includes rest, cold application, compression and elevation. The aim of this treatment is to minimize inflammation, hemorrhage, pain and cellular metabolism during the acute post-injury phase and to optimize the potential for subsequent recovery.

Such initial treatment is often followed by protection of the injured tissues by immobilization for 1-3 weeks after the injury. Immobilization aims to allow healing to begin and to proceed undisturbed and it also prevents re-injury of the joint which often results in longer recovery times and can have long term effects. After tissue healing has begun, typically beyond 3 weeks post injury, controlled mobilization is introduced. At 4-8 weeks pest injury, more vigorous rehabilitation to recover muscle mass and joint function can begin.

Orthopedic repair of severe injuries is often performed as soon as acute swelling and hemorrhage of the injury subsides. However, physicians currently do not have a system or method available to differentiate between acute injury requiring invasive treatment and injuries that will heal sufficiently without such treatment.

It is particularly important to identify injuries that can result in joint deterioration before such deterioration begins. Currently, this kind of information can be obtained only by MRI imaging of the structural components of the joint to determine whether critical structural measures, such as cartilage volume, are being maintained or undergoing progressive degeneration. Typically, imaging is required at intervals of about 1-2 years after injury. Assay of marker proteins in joint fluid can also be used to detect and monitor joint deterioration. However, because such marker assays are generally based on a very limited number of gene products, and the abundance of the products in the fluid can be highly variable, their predictive capacity tends to be very limited.

SUMMARY OF THE PREFERRED EMBODIMENTS

In one aspect, the present invention provides a method for characterizing the quality of the repair response after injury to a joint of a human or veterinary subject. The method includes determining mRNA expression levels of a plurality of genes expressed in a tissue sample taken from an infra-articular region of the joint. In one embodiment, the plurality of genes includes at least the genes listed in Table 1, Table 2 and Table 3. A reparative index score indicative of the quality of the repair response is calculated based on the mRNA expression levels of these genes.

In one embodiment, the mRNA expression levels are determined using a Reverse Transcriptase-Real Time PCR assay. The tissue sample can include cartilage, synovium, meniscal tissue, joint capsule lining, ligaments or combinations of at least two of these materials.

In certain embodiments, calculating the reparative index score includes comparing the mRNA expression levels from the patient tissue with first standard expression levels of the genes and second standard expression levels of the genes, where the first standard expression levels are indicative of a reparative profile and where the second standard expression levels are indicative of a non-reparative profile. The reparative index score is based on relative values of the mRNA expression levels from the patient tissue, the first standard expression levels and the second standard expression levels.

The first standard expression levels can be post-injury expression levels from a wild-type mouse and the second standard expression levels can be post-injury expression levels from a mouse lacking hyaluronan synthase-1. The method can also include applying a correction factor to adjust the relative abundance of the murine levels with respect to the genes expressed in the patient tissue sample.

In other embodiments, the plurality of genes includes at least the genes listed in Table 4, Table 5 and Table 6, or at least the genes listed in Table 7, Table 8 and Table 9. The plurality of genes can also include the genes listed in Table 13, Table 14, and/or Table 15.

Another aspect of the present invention provides a method for treating an injury to a joint of a human or veterinary subject including administrating a therapy depending on the reparative index score as discussed above. In certain embodiments, the therapy is surgical reconstruction, physical therapy, viscosupplementation HA therapy, diet recommendations, life-style change recommendations, anti-inflammatory creams, anti-inflammatory gels or sprays, heat and freeze treatments, non-steroidal anti-inflammatory drugs (NSAIDs), acupuncture, complementary and alternative medicines, steroid injections or steroid tablets.

BRIEF DESCRIPTION OF THE DRAWINGS

FIG. 2 includes bar charts illustrating the relative mRNA abundance for the 22 wound repair genes included In Table 8.

FIG. 3 includes bar charts illustrating the relative mRNA abundance for the 22 inflammation genes included in Table 9.

DETAILED DESCRIPTION OF THE PREFERRED EMBODIMENTS

Definitions

Figure 1:
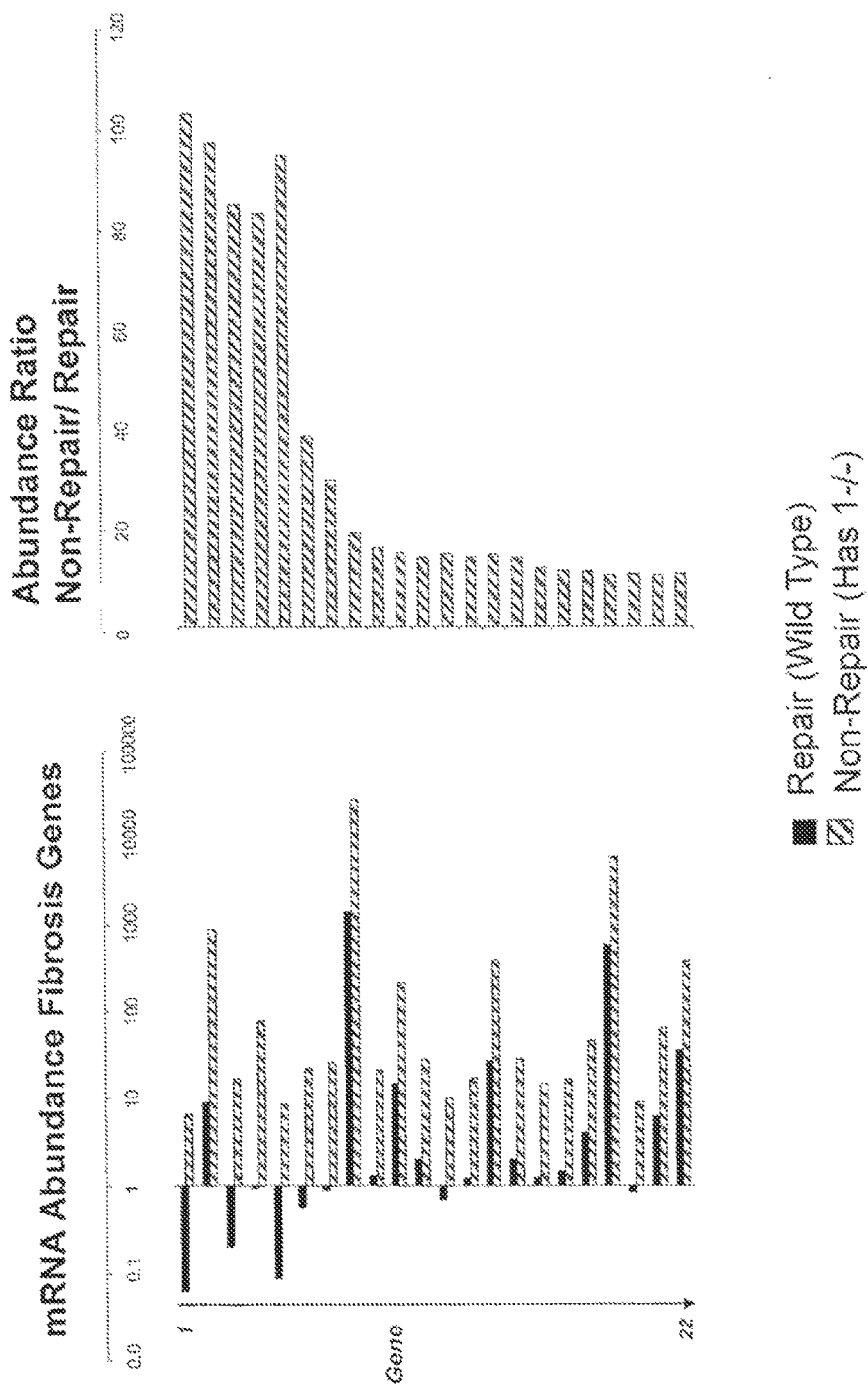
FIG. 1 includes bar charts illustrating the relative mRNA abundance for the 22 fibrosis genes included in Table 7.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it wore individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

As used herein the terms "comprise(s)," "include(s)," "having," "has," "can," and variants thereof, are intended to be open-ended transitional phrases, terms, or words that do not preclude the possibility of additional acts. The present invention also contemplates other embodiments "comprising," "consisting of" and "consisting essentially of," the embodiments or elements presented herein, whether explicitly set forth or not.

Method of Determining the Quality of Repair Response After Joint Injury

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

One aspect of the present invention provides a method of generating a reparative index that is indicative of the quality of the repair response after a joint injury. The joint can be any joint in the body of a human or veterinary subject including, but not limited to, the knee, shoulder, hip, elbow or ankle joints, or a joint of the hand, foot or spine. The method includes a gene expression analysis of a tissue sample taken from the infra-articular space of the joint.

In one embodiment, the method determines changes in the transcriptome of tissue containing stromal and multipotent progenitor cells proximate to the injury site. Specifically, the transcript abundance of a set of "fibroproliferative" and "profibrotic" genes in such joint tissues is predictive of the quality of the long term repair process. Such genes include genes in the fibrosis, cytokine and/or NFkB pathways that are involved in fibrosis, wound healing and inflammation. In a murine model the determination of expression levels of such genes as early as 4 weeks post-injury is predictive of the quality of joint repair which can be expected.

In one embodiment, the tissue sample is obtained from the intra-articular region. As used herein the term "intra-articular" refers to the space inside of a joint between two bones, specifically to the portion of the joint contained by the joint capsule. The sample can include cartilage, synovium, compressed mensical tissue, joint capsule lining, ligaments or combinations of at least two of these materials.

In certain embodiments, the subject is a human subject and the tissue sample is obtained at between 4 weeks and 20 weeks, 4 weeks and 16 weeks, 4 weeks and 12 weeks or 6 weeks and 10 weeks after the injury. In other embodiments multiple tissue samples are obtained, each at a different time after the injury. Such a procedure allows the quality of the repair response to be monitored as time progresses. For example, the quality of natural healing of the joint or the response of the injury to a particular treatment can be determined by observing the changes in gene expression over time. For example, the tissue sample can be obtained during the first arthroscopic (or open joint) evaluation of the injury. In certain cases, depending on the surgeons preferences, a second sample could be obtained at a later time (such as at surgery or at a second arthroscopic evaluation)

The gene expression analysis can be performed by any method known in the art. Methods suitable for such an analysis include, but are not limited to, Northern blot, Nuclease Protection Assay, In Situ Hybridisation and Real Time PCR. In a preferred embodiment, gene expression is measured by quantification of mRNA using Reverse Transcriptase Real Time Polymer Chain Reaction ($RT^2$-PCR.) For example, levels of mRNA can be measured using commercially available products such as the $RT^2$ Profiler PCR Array, available from Qiagen, Inc. (Valencia, Calif.)

In various embodiments, expression levels of genes associated with fibrosis, wound healing and inflammation are measured. In one such embodiment, at least the genes listed in Table 1 (fibrosis genes), Table 2 (wound healing genes) and Table 3 (inflammation genes) are determined in the gene expression analysis. In another embodiment, at least the genes listed in Table 4, Table 5 and Table 6 are determined. In yet another embodiment, at least the genes listed in Table 7, Table 8 and Table 9 are determined. In other embodiments, expression levels of at least some of the genes listed in Tables 13, 14, and 15 are also determined. For example, 10, 20, 40, 50, 60 or 65 of the genes included in Table 13 and/or 5, 10 or 15 of the genes listed in Table 14 can also be determined in the gene expression analysis.

In certain embodiments, the expression levels of the genes discussed above are used to calculate a reparative index score that is indicative of the quality of the repair process after joint injury in a human or veterinary subject. For example, the reparative index can be indicative as to whether the injury displays a wound healing response resulting in repair of the injury (reparative profile) of an aberrant response leading to joint degeneration, fibrosis and/or chronic inflammation (non-reparative profile.)

In one embodiment, the expression levels of genes from a patient tissue sample taken from the region of a joint injury are compared with standard expression levels, for example non-injured expression levels, for the corresponding genes from the same tissue location in the same or a different species. For example, the standard expression levels can be gene expression levels known to be indicative of a reparative profile. In another embodiment, the expression levels from the patient sample are compared with standard expression levels that are indicative of a non-reparative profile. In yet another embodiment, the expression levels from the patient are compared with standard expression levels indicative of both reparative and non-reparative profiles. Where further quantification of the reparative index score is required, additional standards can be included for comparison with the expression levels from the patient.

An exemplary protocol for calculating a reparative index score is described below for the purposes of illustration only. It is not intended that the disclosed methods be limited to this illustrative embodiment.

Expression levels of the required genes selected from those listed in Tables 1-19 and 13-15 are determined in wild type mice (WT) and mice lacking hyaluronan synthase-1 (Has1−/−, MGI:106590) at approximately four weeks post cartilage injury in the knee joint in this injury model, the WT mice display classic wound healing responses in soft tissues, resulting in a reparative response. In comparison, Has1−/− mice show aberrant wound healing responses, leading to fibrosis, chronic inflammation and OA pathology (for example, cartilage degeneration and osteophyte formation.) Pathway-specific gene array analyses in combination with gross morphology, immunochemistry confirms healing response in WT mice but chronic fibrosis and inflammatory status in the joints of Has1−/− mice. At 4 weeks post-injury in a murine model, the transcript abundance of these genes in such joint tissues is predictive of the quality of the long term repair process.

Expression levels for WT mice (repair) and Has1−/− mice (no repair) are shown in Tables 1-9 for 66 genes involved in fibrosis, wound healing or inflammation. These tables also slow the ratio of the expression levels of these genes in WT mice and Has1−/− mice. All of the genes in Tables 1-9 are shown to be up-regulated by at least 7.8 fold in the Has1−/− mice as compared to WT mice. The additional genes are listed in Table 13 are up-regulated by approximately 3-8 fold in Has1−/− mice as compared to WT mice. The genes listed in Table 14 are down-regulated by approximately 3-8 fold in HAs1−/− mice as compared to WT mice.

FIG. 1 illustrates the relative mRNA abundance for the 22 fibrosis genes included in Table 7. Here, expression in Has 1−/− mice is shown to be upgraded up to just over 100 fold. FIG. 2 illustrates the relative mRNA abundance for the 22 wound repair genes included in Table 8. For these genes, expression in Has 1−/− mice is shown to be upgraded up to 200 fold. FIG. 3 illustrates the relative mRNA abundance for the 22 inflammation genes included in Table 9. For these genes, expression in Has 1−/− mice is shown to be upgraded up to just under 400 fold.

In one embodiment, the expression levels of a number of fibrosis, wound healing and inflammation related genes having similar expression levels in WT and Has1−/− mice are measured. For example, such "non-responsive" murine genes can be considered to be genes that are up- or down regulated by less than 3 fold in Has1−/− mice as compared to their levels in WT mice. Table 10 lists the expression levels of 8 such genes.

The expression levels of the non-responsive murine genes, for example the WT mice non-responder genes, are then compared with the expression levels of the corresponding genes in the patient tissue sample. An average gene ratio is calculated. For example, such a calculation for the fibrosis pathway is illustrated in Table 11. This ratio can be used as a murine/human correction factor to normalize expression level differences between the human and murine genes. The WT and Has1−/− expression levels of the murine genes (for example, those genes listed in Tables 1-9, 13-15) are multiplied by the correction factor to generate an equivalent human range for each gene.

A reparative index score can be calculated by, for example, assigning a score of zero to the bottom value of the human range for each gene and a score of 10 to the top value of the human range for each gene, with each intermediate value being scored as appropriate on this scale. A score is assigned for each of the genes measured in the patient sample, for example for each of the 48 genes listed in Tables 4, 5 and 6, and the scores added to give the reparative index score. This total score will range from zero to 160 for each pathway of 16 genes and from zero to 480 for the three combined pathways. A score of zero will be indicative of very good repair and a score of 160 (or 480) as very poor repair. Table 12 illustrates the calculation of the reparative index for a human patient based on the expression levels of the list of six genes in Table 1.

Methods of Treatment

Another aspect of the present invention provides methods for treating an injury to a joint of a human or veterinary subject including administrating a therapy depending on the reparative index score as discussed above. In certain embodiments, the therapy is surgical reconstruction, physical therapy, viscosupplementation HA therapy, diet recommendations or life-style change recommendations. In other embodiments, the treatment includes administration of anti-inflammatory creams, gels or sprays, heat and freeze treatments, non-steroidal anti-inflammatory drugs (NSAIDs), acupuncture, complementary and alternative medicines, steroid injections or steroid tablets.

EXAMPLES

Example 1

Protocol Used to Obtain Tissue Samples for Analysis

Samples for use in the determination of a reparative index for a joint injured patient are typically obtained from one or more of the following: cartilage, synovium, meniscal tissues, joint capsule lining and ligaments (including the ACL, PCL and perimeniscal ligaments.) Samples are usually obtained during the first post-injury arthroscopy. In some cases, where the extent of soft tissue involvement has been determined by MRI or other imaging modalities, the biopsies are taken during surgical repair. Tissue (typically 50 milligrams wet weight) proximate to the injury site, such as perimeniscal synovium in the case of meniscal tears, are immediately placed in RNALater (Qiagen Inc.) and stored at 4° C. for RNA stabilization. RNA (at least 2 micrograms) is analyzed on Qiagen RT$^2$ Profiler PCR arrays for components of the Fibrosis, Wound Healing and Inflammation pathways. Equivalent arrays from other suppliers can also be used. If multiple biopsies are obtained, an index can be generated from each to evaluate the efficacy of the therapies in use.

Example 2

Gene Assay Analysis of a Cartilage Injury Model in Mice

Cartilage injury in the knee joint of wild type mice (C57BL6) and mice lacking hyaluronan synthase-1 (Has1−/−, MGI:108590) is analyzed as described below. The knee joint space is opened and a non-bleeding, partial thickness scalpel wound created in the articular surface of the femoral patellar groove. After lavage of the wound, the joint is closed surgically and the mice are allowed free cage activity with food and water ad libidum.

Knees are dissected (skin and muscle-free) from mice at 0, 3, 7, 14 and 28 days after surgery. The repair/healing status is evaluated by gross morphology, histology and immunohistochemistry with a panel of antibodies against matrix repair and innate inflammatory responses. In addition, a quantitative real time polymerase chain reaction assay is used to quantify the abundance for mRNAs on the Fibrosis, Common cytokine and NFkB array plates (Qiagen Inc., Product Nos. PAMM-225Z, PAMM-021Z and PAMM-120Z.)

Data obtained from gross morphology, histology and immunohistochemistry of the wild-type and Has1−/− mice at each time point are evaluated. Wild-type mice exhibit a transient inflammatory phase and fibrogenic phase that is most evident in the stromal/progenitor cell rich-tissues adjacent to the cartilage injury site. At later times this early response is arrested and recovery from the initial injury is substantial. In contrast, for Has1−/− mice the post-injury soft tissue histopathology is not arrested. Instead it is transformed into further fibro-proliferative responses and classic osteoarthritic changes that include cartilage loss from initially uninjured sites, such as the tibial and patellar surfaces, and osteophyte development on lateral and medial aspects of the femoral groove.

In summary, as assessed by this panel of methods, the reparative response is highly effective in wild-type mice but essentially absent in Has1−/− mice. RT$^2$ PCR array analyses for components of the fibrosis, wound healing and inflammation pathways reveals that wild-type and Has1−/− mice exhibit a markedly different expression of genes in all 3 pathways. 50 genes from each pathway which are found to best discriminate between the 2 genotypes are chosen for use in generation of a reparative index.

In parallel mRNA analyses of murine and human joint tissues, the murine and human models routinely show similar values for the abundance of transcripts for genes of interest. The abundance values for both murine and human samples are controlled internally against the house-keeping gene, glyceraldehyde-3-phosphate dehydrogenase (GAPDH).) This allows standardization of the analysis of human gene expression against murine values obtained under the same assay conditions.

TABLE 1

Transcript Abundance - Fibrosis Pathway: Gene Set 1

| | Gene | Repair | No Repair | NR/R |
|---|---|---|---|---|
| 1 | Inhibin beta E (Inhbe) | 0.1 | 6.5 | 105.0 |
| 2 | Bone morphogenetic protein 1 (Bmp1) | 9.0 | 894.9 | 99.2 |

TABLE 1-continued

Transcript Abundance - Fibrosis Pathway: Gene Set 1

| | Gene | Repair | No Repair | NR/R |
|---|---|---|---|---|
| 3 | Interferon gamma (Ifng) | 0.2 | 17.1 | 86.4 |
| 4 | Fibrosin (Fbrs) | 0.9 | 78.8 | 84.6 |
| 5 | Interleukin 11 (Il11) | 0.09 | 6.54 | 96.7 |
| 6 | Endothelin 1 (Edn1) | 0.6 | 22.3 | 39.0 |

TABLE 2

Transcript Abundance - Wound Healing Pathway: Gene Set 1

| | Gene | Repair | No Repair | NR/R |
|---|---|---|---|---|
| 1 | Interleukin 2 (Il2) | 0.1 | 17.2 | 207.4 |
| 2 | Colony stimulating factor 2 (granulocyte-macrophage) (Csf2) | 0.0 | 7.1 | 206.7 |
| 3 | Matrix metallopeptidase 1a (interstitial collagenase) (Mmp1a) | 0.1 | 17.2 | 190.8 |
| 4 | Plasminogen (Plg) | 0.1 | 8.9 | 142.4 |
| 5 | Fibroblast growth factor 10 (Fgf10) | 0.2 | 18.5 | 82.7 |
| 6 | Interleukin 6 (IL6) | 0.4 | 18.3 | 51.3 |

TABLE 3

Transcript Abundance - Inflammation Pathway: Gene Set 1

| | Gene | Repair | No Repair | NR/R |
|---|---|---|---|---|
| 1 | Synaptosomal-associated protein 25 (Snap25) | 0.06 | 15.23 | 244.8 |
| 2 | Interleukin 20 (Il20) | 0.06 | 12.21 | 196.2 |
| 3 | Chemokine (C-X-C motif) ligand 3 (Cxcl3) | 0.06 | 15.01 | 180.3 |
| 4 | Interleukin 21 (Il21) | 0.06 | 9.31 | 149.6 |
| 5 | Interleukin 3 (Il3) | 0.06 | 11.06 | 177.8 |
| 6 | Interferon beta 1, fibroblast (Ifnb1) | 0.06 | 22.61 | 363.4 |

TABLE 4

Transcript Abundance Fibrosis Pathway Gene Set 2

| | Gene | Repair | No Repair | NR/R |
|---|---|---|---|---|
| 1 | Inhibin beta E (Inhbe) | 0.1 | 6.5 | 105.0 |
| 2 | Bone morphogenetic protein 1 (Bmp1) | 9.0 | 894.9 | 99.2 |
| 3 | Interferon gamma (Ifng) | 0.2 | 17.1 | 86.4 |
| 4 | Fibrosin (Fbrs) | 0.9 | 78.8 | 84.6 |
| 5 | Interluekin 11 (Il11) | 0.09 | 8.54 | 96.7 |
| 6 | Endothelin 1 (Edn1) | 0.6 | 22.3 | 39.0 |
| 7 | Chemokine (C-C motif) ligand 3 (Ccl3) | 0.9 | 25.9 | 30.0 |
| 8 | Collagen, type III, alpha 1 (Col3a1) | 1435 | 27331 | 19.0 |
| 9 | Interleukin 13 receptor, alpha 2 (Il13ra2) | 1.3 | 21.0 | 16.1 |
| 10 | Matrix metallopeptidase 3 (Mmp3) | 14.7 | 218.8 | 14.9 |

TABLE 4-continued

Transcript Abundance Fibrosis Pathway Gene Set 2

| | Gene | Repair | No Repair | NR/R |
|---|---|---|---|---|
| 11 | Chemokine (C-C motif) ligand 12 (Ccl12) | 2.0 | 28.3 | 14.0 |
| 12 | Fas ligand (TNF superfamily, member 6) (Fasl) | 0.7 | 10.1 | 14.8 |
| 13 | TGFB-induced factor homeobox 1 (Tgif1) | 1.2 | 17.1 | 14.0 |
| 14 | Caveolin 1, caveolae protein (Cav1) | 26.5 | 389.3 | 14.7 |
| 15 | Chemokine (C-C motif) ligand 11 (Ccl11) | 1.3 | 14.7 | 11.6 |

TABLE 5

Transcript Abundance Wound Healing Pathway Gene Set 2

| | Gene | Repair | No Repair | NR/R |
|---|---|---|---|---|
| 1 | Interleukin 2 (Il2) | 0.1 | 17.2 | 207.4 |
| 2 | Colony stimulating factor (granulocyte-macrophage) (Csf2) | 0.0 | 7.1 | 206.7 |
| 3 | Matrix metallopeptidase 1a (interstitial collagenase) (Mmp1a) | 0.1 | 17.2 | 190.8 |
| 4 | Plasminogen (Plg) | 0.1 | 8.9 | 142.4 |
| 5 | Fibroblast growth factor 10 (Fgf10) | 0.2 | 18.5 | 82.7 |
| 6 | Interleukin 6 (Il6) | 0.4 | 18.3 | 51.3 |
| 7 | Interleukin 10 (Il10) | 0.8 | 30.6 | 39.9 |
| 8 | Macrophage migration inhibitory factor (Mif) | 54.7 | 1893.3 | 34.6 |
| 9 | Matrix metallopeptidase 2 (Mmp2) | 152.2 | 3183.6 | 20.9 |
| 10 | Epidermal growth factor (Egf) | 0.7 | 13.8 | 19.6 |
| 11 | Integrin beta 8 (Itgb8) | 0.6 | 10.3 | 17.5 |
| 12 | Prostaglandin-endoperoxide synthase 2 (Ptgs2) | 1.2 | 21.2 | 17.5 |
| 13 | Selectin, platelet (Plat) | 1.8 | 27.4 | 15.5 |
| 14 | Integrin beta 6 (Itgb6) | 2.1 | 28.6 | 13.8 |
| 15 | Tissue inhibitor of metalloproteinase 1 (Timp1) | 0.1 | 1.3 | 13.4 |
| 16 | Colony stimulating factor 3 (granulocyte) (Csf3) | 0.2 | 2.6 | 12.6 |

TABLE 6

Transcript Abundance Inflammation Pathway Gene Set 2

| | Gene | Repair | No Repair | NR/R |
|---|---|---|---|---|
| 1 | Synaptosomal-associated protein 25 (Snap25) | 0.06 | 15.23 | 244.8 |
| 2 | Interleukin 20 (Il20) | 0.06 | 12.21 | 196.2 |
| 3 | Chemokine (C-X-C motif) ligand 3 (Cxcl3) | 0.08 | 15.01 | 180.3 |
| 4 | Interleukin 21 (Il21) | 0.06 | 9.31 | 149.6 |
| 5 | Interleukin 3 (Il3) | 0.06 | 11.06 | 177.8 |
| 6 | Interferon beta 1, fibroblast (Ifnb1) | 0.06 | 22.61 | 363.4 |
| 7 | Chemokine (C-C motif) ligand 22 (Ccl22) | 0.1 | 8.8 | 83.3 |
| 8 | Interleukin 12B (Il12b) | 0.2 | 13.6 | 71.7 |
| 9 | Complement component 4A (Rodgers blood group) (C4a) | 0.2 | 3.9 | 22.6 |
| 10 | Chemokine (C-X-C motif) ligand 1 (Cxcl1) | 0.3 | 11.2 | 34.9 |
| 11 | Interleukin 24 (Il24) | 0.4 | 16.1 | 37.9 |
| 12 | Leukemia inhibitory factor (Lif) | 0.5 | 17.9 | 36.6 |
| 13 | Fas ligand (TNF superfamily, member 6) (Fasl) | 1.7 | 28.6 | 17.2 |
| 14 | Interleukin 18 (Il18) | 10.5 | 116.9 | 11.2 |
| 15 | Interleukin 16 (Il16) | 3.7 | 50.2 | 13.5 |
| 16 | Early growth response 2 (Egr2) | 8.1 | 85.0 | 10.5 |

TABLE 7

Transcript Abundance Fibrosis Pathway Gene Set 3

| | Gene | Repair | No Repair | NR/R |
|---|---|---|---|---|
| 1 | Inhibin beta E (Inhbe) | 0.1 | 6.5 | 105.0 |
| 2 | Bone morphogenetic protein 1 (Bmp1) | 9.0 | 894.9 | 99.2 |
| 3 | Interferon gamma (Ifng) | 0.2 | 17.1 | 86.4 |
| 4 | Fibrosin (Fbrs) | 0.9 | 78.8 | 84.6 |
| 5 | Interleukin 11 (Il11) | 0.09 | 8.54 | 96.7 |
| 6 | Endothelin 1 (Edn1) | 0.6 | 22.3 | 39.0 |

TABLE 7-continued

Transcript Abundance Fibrosis Pathway Gene Set 3

| | Gene | Repair | No Repair | NR/R |
|---|---|---|---|---|
| 7 | Chemokine (C-C motif) ligand 3 (Ccl3) | 0.9 | 25.9 | 30.0 |
| 8 | Collagen, type III, alpha 1 (Col3a1) | 1435 | 27331 | 19.0 |
| 9 | Interleukin 13 receptor, alpha 2 (Il13ra2) | 1.3 | 21.0 | 16.1 |
| 10 | Matrix metallopeptidase 3 (Mmp3) | 14.7 | 218.8 | 14.9 |
| 11 | Chemokine (C-C motif) ligand 12 (Ccl12) | 2.0 | 28.3 | 14.0 |
| 12 | Fas ligand (TNF superfamily, member 6) (Fasl) | 0.7 | 10.1 | 14.8 |
| 13 | TGFB-induced factor homeobox 1 (Tgif1) | 1.2 | 17.1 | 14.0 |
| 14 | Caveolin 1, caveolae protein (Cav1) | 26.5 | 389.3 | 14.7 |
| 15 | Chemokine (C-C motif) ligand 12 (Ccl12) | 2.0 | 28.3 | 14.0 |
| 16 | Chemokine (C-C motif) ligand 11 (Ccl11) | 1.3 | 14.7 | 11.8 |
| 17 | Snail homolog 1 (*Drosophila*) (Snai1) | 1.5 | 16.7 | 11.4 |
| 18 | Transforming growth factor, beta 2 (Tgfb2) | 4.0 | 44.7 | 11.2 |
| 19 | Connective tissue growth factor (Ctgf) | 585.0 | 6138.4 | 10.5 |
| 20 | Bone morphogenetic protein 7 (Bmp7) | 0.8 | 9.0 | 10.7 |
| 21 | Transforming growth factor, beta 3 (Tgfb3) | 6.2 | 64.7 | 10.5 |
| 22 | Tissue inhibitor of metalloproteinase 3 (Timp3) | 36.0 | 380.2 | 10.6 |

TABLE 8

Transcript Abundance Wound Healing Pathway Gene Set 3

| | Gene | Repair | No Repair | NR/R |
|---|---|---|---|---|
| 1 | Interleukin 2 (Il2) | 0.1 | 17.2 | 207.4 |
| 2 | Colony stimulating factor 2 (granulocyte-macrophage) (Csf2) | 0.0 | 7.1 | 206.7 |
| 3 | Matrix metallopeptidase 1a (interstitial collagenase) (Mmp1a) | 0.1 | 17.2 | 190.8 |
| 4 | Plasminogen (Plg) | 0.1 | 8.9 | 142.4 |
| 5 | Fibroblast growth factor 10 (Fgf10) | 0.2 | 18.5 | 82.7 |
| 6 | Interleukin 6 (Il6) | 0.4 | 18.3 | 51.3 |
| 7 | Interleukin 10 (Il10) | 0.8 | 30.6 | 39.9 |
| 8 | Macrophage migration inhibitory factor (Mif) | 54.7 | 1893.3 | 34.6 |
| 9 | Matrix metallopeptidase 2 (Mmp2) | 152.2 | 3183.6 | 20.9 |
| 10 | Epidermal growth factor (Egf) | 0.7 | 13.8 | 19.6 |
| 11 | Integrin beta 8 (Itgb8) | 0.6 | 10.3 | 17.5 |
| 12 | Prostaglandin-endoperoxide synthase 2 (Ptgs2) | 1.2 | 21.2 | 17.5 |
| 13 | Selectin, platelet (Plat) | 1.8 | 27.4 | 15.5 |
| 14 | Integrin beta 6 (Itgb6) | 2.1 | 28.6 | 13.8 |
| 15 | Tissue inhibitor of metalloproteinase 1 (Timp1) | 0.1 | 1.3 | 13.4 |
| 16 | Colony stimulating factor 3 (granulocyte) (Csf3) | 0.2 | 2.6 | 12.6 |
| 17 | Thrombospondin 2 (Thbs2) | 55.8 | 675.4 | 12.1 |
| 18 | Integrin alpha 3 (Itgat3) | 0.7 | 8.0 | 12.0 |
| 19 | Integrin beta 5 (Itgb5) | 19.7 | 210.7 | 10.7 |
| 20 | Versican V1 isoform (Vcan V1) | 0.1 | 0.5 | 9.0 |
| 21 | Hepatocyte growth factor (Hgf) | 8.4 | 72.0 | 8.6 |
| 22 | Vascular endothelial growth factor A (Vegfa) | 6.0 | 47.0 | 7.8 |

TABLE 9

Transcript Abundance Inflammation Pathway Gene Set 3

| | Gene | Repair | No Repair | NR/R |
|---|---|---|---|---|
| 1 | Synaptosomal-associated protein 25 (Snap25) | 0.06 | 15.23 | 244.8 |
| 2 | Interleukin 20 (Il20) | 0.06 | 12.21 | 196.2 |
| 3 | Chemokine (C-X-C motif) ligand 3 (Cxcl3) | 0.08 | 15.01 | 180.3 |
| 4 | Interleukin 21 (Il21) | 0.06 | 9.31 | 149.6 |
| 5 | Interleukin 3 (Il3) | 0.06 | 11.06 | 177.8 |
| 6 | Interferon beta 1, fibroblast (Ifnb1) | 0.06 | 22.61 | 363.4 |

TABLE 9-continued

Transcript Abundance Inflammation Pathway Gene Set 3

| | Gene | Repair | No Repair | NR/R |
|---|---|---|---|---|
| 7 | Chemokine (C-C motif) ligand 22 (Ccl22) | 0.1 | 8.8 | 83.3 |
| 8 | Interleukin 12B (Il12b) | 0.2 | 13.6 | 71.7 |
| 9 | Complement component 4A (Rodgers blood group) (C4a) | 0.2 | 3.9 | 22.6 |
| 10 | Chemokine (C-X-C motif) ligand 1 (Cxcl1) | 0.3 | 11.2 | 34.9 |
| 11 | Interleukin 24 (Il24) | 0.4 | 16.1 | 37.9 |
| 12 | Leukemia inhibitory factor (Lif) | 0.5 | 17.9 | 36.6 |
| 13 | Fas ligand (TNF superfamily, member 6) (FasL) | 1.7 | 28.6 | 17.2 |
| 14 | Interleukin 18 (Il18) | 10.5 | 116.9 | 11.2 |
| 15 | Interleukin 16 (Il16) | 3.7 | 50.2 | 13.5 |
| 16 | Early growth response 2 (Egr2) | 8.1 | 85.0 | 10.5 |
| 17 | B-cell leukemia/lymphoma 2 related protein A1a (Bcl2a1a) | 5.2 | 54.8 | 10.5 |
| 18 | Interferon alpha 4 (Infa4) | 0.1 | 17.7 | 9.6 |
| 19 | Interleukin 1 alpha (Il1a) | 7.2 | 69.0 | 9.6 |
| 20 | Adrenomedullin (Adm) | 0.5 | 4.2 | 9.0 |

TABLE 10

Normalizing Gene Set 1

| Gene | Repair | No Repair | NR/R |
|---|---|---|---|
| Thymoma viral proto-oncogene 1 (Akt1) | 69.0 | 113.1 | 1.6 |
| Colony stimulating factor 2 receptor, beta, low-affinity (granulocyte-macrophage) (Csf2rb2) | 32.7 | 67.0 | 2.0 |
| Interferon regulatory factor 1 (Irf1) | 78.1 | 163.1 | 2.1 |
| Lymphotoxin B (Ltb) | 20.3 | 33.9 | 1.7 |
| Signal transducer and activator of transcription 1 (Stat1) | 100.2 | 171.2 | 1.7 |
| Signal transducer and activator of transcription 3 (Stat3) | 18.3 | 50.6 | 2.8 |
| Tumor necrosis factor (Tnf) | 7.6 | 17.3 | 2.3 |
| Tumor necrosis factor receptor superfamily, member 1b (Tnfrsf1b) | 23.5 | 44.7 | 1.9 |

TABLE 11

Calculation of Fibrosis Pathway Index: Ratio of non-responder genes

| | Data from Patient A for non-responder genes | Patient A/ Murine for non-responder genes |
|---|---|---|
| Thymoma viral proto-oncogene 1 (Akt1) | 31 | 0.45 |
| Colony stimulating factor 2 receptor, beta, low-affinity (granulocyte-macrophage) (Csf2rb) | 25 | 0.76 |
| Interferon regulatory factor 1 (Irf1) | 37 | 0.47 |
| Lymphotoxin B (Ltb) | 16 | 0.8 |
| Signal transducer and activator of transcription 1 (Stat1) | 45 | 0.45 |
| Signal transducer and activator of transcription 3 (Stat3) | 5.0 | 0.28 |
| Tumor necrosis factor (Tnf) | 2.1 | 0.28 |
| Tumor necrosis factor receptor superfamily, member 1b (Tnfrsf1b) | 18 | 0.75 |
| Average ratio | | 0.53 |

TABLE 12

Calculation of Fibrosis Pathway Index for a Human Patient

| Gene | Transcript Abundance Fibrosis Pathway (murine) Repair | Transcript Abundance Fibrosis Pathway (murine) No Repair | Transcript Abundance Fibrosis Pathway (human) Repair | Transcript Abundance Fibrosis Pathway (human) No Repair | Patient A - Transcript Abundance Fibrosis Pathway | Patient A - Index Score |
|---|---|---|---|---|---|---|
| 1 Inhibin beta E (Inhbe) | 0.1 | 6.5 | 0.053 | 3.4 | 4.6 | 10 |
| 2 Bone morphogenetic protein 1 (Bmp1) | 9.0 | 894.9 | 4.7 | 464 | 261 | 6 |
| 3 Interferon gamma (Ifng) | 0.2 | 17.1 | 0.12 | 9.1 | 7.9 | 8 |
| 4 Fibrosin (Fbrs) | 0.9 | 78.8 | 0.47 | 42 | 23 | 5 |
| 5 Interleukin 11 (Il11) | 0.09 | 8.54 | 0.048 | 4.6 | 4.3 | 9 |
| 6 Endothelin 1 (Edn1) | 0.6 | 22.3 | 0.34 | 13.2 | 3.6 | 3 |
| Total Score | | | | | | 41 |

TABLE 13

Additional Genes Included in the Fibrosis, Wound Healing or Inflammation Pathways - Set 1

| | Gene |
|---|---|
| 1 | Adrenomedullin (Adm) |
| 2 | Baculoviral IAP repeat-containing 2 (Birc2) |
| 3 | Baculoviral IAP repeat-containing 3 (Birc3) |
| 4 | Chemokine (C-C motif) ligand 12 (Ccl12) |
| 5 | Chemokine (C-C motif) ligand 5 (Ccl5) |
| 6 | Cyclin D1 (Ccnd1) |
| 7 | Chemokine (C-C motifi receptor 5 (Ccr5) |
| 8 | CD80 antigen (Cd80) |
| 9 | Epidermal growth factor receptor (Egfr) |
| 10 | Coagulation factor III (F3) |
| 11 | Coagulation factor VIII (F8) |
| 12 | Growth arrest and DNA-damage-inducible 45 beta (Gadd45b) |
| 13 | Interleukin 1 receptor, type II (Il1r2) |
| 14 | Interleukin 1 receptor antagonist (Il1rn) |
| 15 | Interleukin 2 receptor, alpha chain (Il2ra) |
| 16 | Interleukin 15 (Il15) |
| 17 | Interleukin 18 (Il18) |
| 18 | Interleukin 1 family, member 9 (Il1f9) |
| 19 | Interleukin 24 (Il24) |
| 20 | Interleukin 27 (Il27) |
| 21 | Inhibin beta-A (Inhba) |
| 22 | Left right determination factor 1 (Lefty1) |
| 23 | Lymphotoxin B (Ltb) |
| 24 | Tumor necrosis factor (ligand) superfamily, member 13 (Tnfsf13) |
| 25 | Angiotensinogen (serpin peptidase inhibitor, clade A, member 8) (Agt) |
| 26 | Chemokine (C-C motif) receptor 2 (Ccr2) |
| 27 | CCAAT/enhancer binding protein (C/EBP), beta (Cebpb) |
| 28 | Chemokine (C-X-C motif) receptor 4 (Cxcr4) |
| 29 | Endoglin (Eng) |
| 30 | Plasminogen activator, urokinase (Plau) |
| 31 | Serine (or cysteine) peptidase inhibitor, clade A, member 1a (Serpina1a) |
| 32 | Serine (or cysteine) peptidase inhibitor, clade E, member 1 (Serpine1) |

TABLE 13-continued

Additional Genes Included in the Fibrosis, Wound Healing or Inflammation Pathways - Set 1

| | Gene |
|---|---|
| 33 | Serine (or cysteine) peptidase inhibitor, clade H, member 1 (Serpinh1) |
| 34 | MAD homolog 2 (Drosophila) (Smad2) |
| 35 | MAD homolog 3 (Drosophila) (Smad3) |
| 36 | MAD homolog 4 (Drosophila) (Smad4) |
| 37 | MAD homolog 6 (Drosophila) (Smad6) |
| 38 | MAD homolog 7 (Drosophila) (Smad7) |
| 39 | Signal transducer and activator of transcription 1 (Stat1) |
| 40 | Mitogen-activated protein kinase kinase 6 (Map2k6) |
| 41 | Myelocytomatosis oncogene (Myc) |
| 42 | Nuclear factor of kappa light polypeptide gene enhancer in B-cells 1, p105 (Nfkb1) |
| 43 | NAD(P)H dehydrogenase, quinone 1 (Nqo1) |
| 44 | Avian reticuloendotheliosis viral (v-rel) oncogene related B (Relb) |
| 45 | Selectin, endothelial cell (Sele) |
| 46 | Superoxide dismutase 2, mitochondrial (Sod2) |
| 47 | Signal transducer and activator of transcription 5B (Stat5b) |
| 48 | Tumor necrosis factor (ligand) superfamily, member 10 (Tnfsf10) |
| 49 | Integrin beta 3 (Itgb3) |
| 50 | Jun oncogene (Jun) |
| 51 | Latent transforming growth factor beta binding protein 1 (Ltbp1) |
| 52 | Matrix metallopeptidase 9 (Mmp9) |
| 53 | Tissue inhibitor of metalloproteinase 4 (Timp4) |

TABLE 14

Additional Genes Included in the Fibrosis, Wound Healing or Inflammation Pathways - Set 2

| | Gene |
|---|---|
| 1 | Colony stimulating factor 2 (granulocyte-macrophage) (Csf2) |
| 2 | Interleukin 4 (Il4) |
| 3 | Insulin II (Ins2) |
| 4 | Bone morphogenetic protein 8b (Bmp8b) |
| 5 | Cardiotrophin 2 (Ctf2) |
| 6 | Growth differentiation factor 15 (Gdf15) |
| 7 | Interferon alpha 2 (Ifna2) |
| 8 | Interleukin 13 (Il13) |
| 9 | Interleukin 17C (Il17c) |
| 10 | Interleukin 25 (Il25) |
| 11 | Interleukin 9 (Il9) |
| 12 | Tumor necrosis factor (ligand) superfamily, member 18 (Tnfsf18) |
| 13 | Tumor necrosis factor (ligand) superfamily, member 4 (Tnfsf4) |
| 14 | Interleukin 13 (Il13) |
| 15 | Interleukin 4 (Il4) |

TABLE 15

Extracellular Matrix and Hyaluronan Network-Associated Genes Related to the Fibrosis, Wound Healing or Inflammation Pathways

| | Gene |
|---|---|
| 1 | Aggrecan (Acan) |
| 2 | Alpha-1-Microglobulin/Bikunin Precursor (Ambp) |
| 3 | Collagen, type I, alpha 1 (Col1a1) |
| 4 | Collagen, type I, alpha 2 (Col1a2) |
| 5 | Collagen, type II, alpha 1 (Col2a1) |
| 6 | Collagen, type III, alpha 1 (Col3a1) |
| 7 | Hyaluronan synthase 1 (Has1) |
| 8 | Hyaluronan synthase 2 (Has2) |
| 9 | Hyaluronan synthase 3 (Has3) |
| 10 | Inter-Alpha-Trypsin Inhibitor Heavy Chain 1 (Itih1) |
| 11 | Inter-Alpha-Trypsin Inhibitor Heavy Chain 2 (Itih2) |
| 12 | Stabilin 2 (Stab2) |
| 13 | Tumor Necrosis Factor, Alpha-Induced Protein 6 (Tnfaip6) |
| 14 | Versican (Vcan) |

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A method for treating an injury to a joint of a human or veterinary subject, comprising: administrating a therapy selected from the group consisting of surgical reconstruction and viscosupplementation HA therapy, wherein the therapy is administered to the subject having a non-reparative response to the injury as indicated by an elevated mRNA expression level of a plurality of genes comprising at least the genes Inhibin beta E (Inhbe), Bone morphogenetic protein 1 (Bmp1), Interferon gamma (Ifng), Fibrosin (Fbrs), Interleukin 11 (Il11), Endothelin 1 (Edn1), Interleukin 2 (Il2), Colony stimulating factor 2 (granulocyte-macrophage) (Csf2), Matrix metallopeptidase 1a (interstitial collagenase) (Mmp1a), Plasminogen (Plg), Fibroblast growth factor 10 (Fgf10), Interleukin 6 (Il6), Synaptosomal-associated protein 25 (Snap25), Interleukin 20 (Il20), Chemokine (C-X-C motif) ligand 3 (Cxcl3), Interleukin 21 (Il21), Interleukin 3 (Il3) and Interferon beta 1 fibroblast (Ifnb1);

wherein the mRNA expression levels are determined in a tissue sample taken from an intra-articular region of the joint.

2. The method of claim 1, wherein the tissue sample comprises material selected from the group consisting of cartilage, synovium, meniscal tissue, joint capsule lining, ligaments and combinations of at least two of these materials.

3. The method of claim 1, wherein the subject is a human subject and wherein the mRNA expression levels are determined at between 4 weeks and 12 weeks post-injury.

4. The method of claim 1, wherein the elevated mRNA expression levels are compared with first standard expression levels of the plurality of genes and second standard expression levels of the plurality of genes, wherein the first standard expression levels are indicative of a reparative profile, wherein the second standard expression levels are indicative of a non-reparative profile, and wherein a reparative index score is calculated based on the comparing.

5. The method of claim 1, wherein the plurality of genes comprises at least the genes Inhibin beta E (Inhbe), Bone morphogenetic protein 1 (Bmp1), Interferon gamma (Ifng), Fibrosin (Fbrs), Interleukin 11 (Il11), Endothelin 1 (Edn1), Chemokine (C-C motif) ligand 3 (Ccl3), Collagen, type III, alpha 1 (Col3a1), Interleukin 13 receptor, alpha 2 (Il13ra2), Matrix metallopeptidase 3 (Mmp3), Chemokine (C-C motif) ligand 12 (Ccl12), Fas ligand (TNF superfamily, member 6) (Fasl), TGFB-induced factor homeobox 1 (Tgif1), Caveolin 1, caveolae protein (Cav1), Chemokine (C-C motif) ligand 11 (Ccl11), Interleukin 2 (Il2), Colony stimulating factor 2 (granulocyte-macrophage) (Csf2), Matrix metallopeptidase 1a (interstitial collagenase) (Mmp1a), Plasminogen (Plg), Fibroblast growth factor 10 (Fgf10), Interleukin 6 (Il6), Interleukin 10 (Il10), Macrophage migration inhibitory factor (Mif), Matrix metallopeptidase 2 (Mmp2), Epidermal growth factor (Egf), Integrin beta 8 (Itgb8), Prostaglandin-endoperoxide synthase 2 (Ptgs2), Selectin, platelet (Plat), Integrin beta 6 (Itgb6), Tissue inhibitor of metalloproteinase 1 (Timp1), Colony stimulating factor 3 (granulocyte) (Csf3), Synaptosomal-associated protein 25 (Snap25), Interleukin 20 (Il20), Chemokine (C-X-C motif) ligand 3 (Cxcl3), Interleukin 21 (Il21), Interleukin 3 (Il3), Interferon beta 1, fibroblast (Ifnb1), Chemokine (C-C motif) ligand 22 (Ccl22), Interleukin 12B (Il12b), Complement component 4A (Rodgers blood group) (C4a), Chemokine (C-X-C motif) ligand 1 (Cxcl1), Interleukin 24 (Il24), Leukemia inhibitory factor (Lif), Fas ligand (TNF superfamily, member 6) (Fasl), Interleukin 18 (Il18), Interleukin 16 (Il16) and Early growth response 2 (Egr2).

6. The method of claim 1, wherein the plurality of genes comprises at least the genes Inhibin beta E (Inhbe), Bone morphogenetic protein 1 (Bmp1), Interferon gamma (Ifng), Fibrosin (Fbrs), Interleukin 11 (Il11), Endothelin 1 (Edn1), Chemokine (C-C motif) ligand 3 (Ccl3), Collagen, type III, alpha 1 (Col3a1), Interleukin 13 receptor, alpha 2 (Il13ra2), Matrix metallopeptidase 3 (Mmp3), Chemokine (C-C motif) ligand 12 (Ccl12), Fas ligand (TNF superfamily, member 6) (Fasl), TGFB-induced factor homeobox 1 (Tgif1), Caveolin 1, caveolae protein (Cav1), Chemokine (C-C motif) ligand 12 (Ccl12), Chemokine (C-C motif) ligand 11 (Ccl11), Snail homolog 1 (*Drosophila*) (Snail1), Transforming growth factor, beta 2 (Tgfb2), Connective tissue growth factor (Ctgf), Bone morphogenetic protein 7 (Bmp7), Transforming growth factor, beta 3 (Tgfb3), Tissue inhibitor of metallo-proteinase 3 (Timp3), Interleukin 2 (Il2), Colony stimulating factor 2 (granulocyte-macrophage) (Csf2), Matrix metallopeptidase 1a (interstitial collagenase) (Mmp1a), Plasminogen (Plg), Fibroblast growth factor 10 (Fgf10), Interleukin 6 (Il6), Interleukin 10 (Il10), Macrophage migration inhibitory factor (Mif), Matrix metallopeptidase 2 (Mmp2), Epidermal growth factor (Egf), Integrin beta 8 (Itgb8), Prostaglandin-endoperoxide synthase 2 (Ptgs2), Selectin, platelet (Plat), Integrin beta 6 (Itgb6), Tissue inhibitor of metalloproteinase 1 (Timp1), Colony stimulating factor 3 (granulocyte) (Csf3), Thrombospondin 2 (Thbs2), Integrin alpha 3 (Itga3), Integrin beta 5 (Itgb5), Versican V1 isoform (Vcan V1), Hepatocyte growth factor (Hgf), Vascular endothelial growth factor A (Vegfa), Synaptosomal-associated protein 25 (Snap25), Interleukin 20 (Il20, Chemokine (C-X-C motif) ligand 3 (Cxcl3), Interleukin 21 (Il21), Interleukin 3 (Il3), Interferon beta 1, fibroblast (Ifnb1), Chemokine (C-C motif) ligand 22 (Ccl22), Interleukin 12B (Il12b), Complement component 4A (Rodgers blood group) (C4a), Chemokine (C-X-C motif) ligand 1 (Cxcl1), Interleukin 24 (Il24), Leukemia inhibitory factor (Lif), Fas ligand (TNF superfamily, member 6) (FasL), Interleukin 18 (Il18), Interleukin 16 (Il16), Early growth response 2 (Egr2), B-cell leukemia/lymphoma 2 related protein A1a (Bcl2a1a), Interferon alpha 4 (Ifna4), Interleukin 1 alpha (Il1a) and Adrenomedullin (Adm).

7. The method of claim 6, wherein the plurality of genes further comprises the genes Adrenomedullin (Adm), Baculoviral IAP repeat-containing 2 (Birc2), Baculoviral IAP repeat-containing 3 (Birc3), Chemokine (C-C motif) ligand 12 (Ccl12), Chemokine (C-C motif) ligand 5 (Ccl5), Cyclin D1 (Ccnd1), Chemokine (C-C motif) receptor 5 (Ccr5), CD80 antigen (Cd80), Epidermal growth factor receptor (Egfr), Coagulation factor III (F3), Coagulation factor VIII (F8), Growth arrest and DNA-damage-inducible 45 beta (Gadd45b), Interleukin 1 receptor, type II (Il1r2), Interleukin 1 receptor antagonist (Il1rn), Interleukin 2 receptor, alpha chain (Il2ra), Interleukin 15 (Il15), Interleukin 18 (Il18), Interleukin 1 family, member 9 (Il1f9), Interleukin 24 (Il24), Interleukin 27 (Il27), Inhibin beta-A (Inhba), Left right determination factor 1 (Lefty1), Lymphotoxin B (Ltb), Tumor necrosis factor (ligand) superfamily, member 13 (Tnfsf13), Angiotensinogen (serpin peptidase inhibitor, Glade A, member 8) (Agt), Chemokine (C-C motif) receptor 2 (Ccr2), CCAAT/enhancer binding protein (C/EBP), beta (Cebpb), Chemokine (C-X-C motif) receptor 4 (Cxcr4), Endoglin (Eng), Plasminogen activator, urokinase (Plau), Serine (or cysteine) peptidase inhibitor, Glade A, member 1a (Serpina1a), Serine (or cysteine), peptidase inhibitor, clade E, member 1 (Serpine1), Serine (or cysteine) peptidase inhibitor, clade H, member 1 (Serpinh1), MAD homolog 2 (*Drosophila*) (Smad2), MAD homolog 3 (*Drosophila*) (Smad3), MAD homolog 4 (*Drosophila*) (Smad4), MAD homolog 6 (*Drosophila*) (Smad6), MAD homolog 7 (*Drosophila*) (Smad7), Signal transducer and activator of transcription 1 (Stat1), Mitogen-activated protein kinase kinase 6 (Map2k6) Myelocytomatosis oncogene (Myc), Nuclear factor of kappa light polypeptide gene enhancer in B-cells 1, p105 (Nfkb1), NAD(P)H dehydrogenase, quinone 1 (Nqo1), Avian reticuloendotheliosis viral (v-rel) oncogene related B (Relb), Selectin, endothelial cell (Sele), Superoxide dismutase 2, mitochondrial (Sod2), Signal transducer and activator of transcription 5B (Stat5b), Tumor necrosis factor (ligand) superfamily, member 10 (Tnfsf10), Integrin beta 3 (Itgb3), Jun oncogene (Jun), Latent transforming growth factor beta binding protein 1 (Ltbp1), Matrix metallopeptidase 9 (Mmp9) and Tissue inhibitor of metalloproteinase 4 (Timp4).

8. The method of claim 6, wherein the plurality of genes further comprises the genes Colony stimulating factor 2 (granulocyte-macrophage) (Csf2), Interleukin 4 (Il4), Insulin II (Ins2), Bone morphogenetic protein 8b (Bmp8b), Cardiotrophin 2 (Ctf2), Growth differentiation factor 15 (Gdf15), Interferon alpha 2 (Ifna2), Interleukin 13 (Il13), Interleukin 17C (Il17c), Interleukin 25 (Il25), Interleukin 9 (Il9), Tumor necrosis factor (ligand) superfamily, member 18 (Tnfsf18), Tumor necrosis factor (ligand) superfamily, member 4 (Tnfsf4), Interleukin 13 (Il13) and Interleukin 4 (Il4).

9. The method of claim 6, wherein the plurality of genes further comprises the genes Aggrecan (Acan), Alpha-1-Microglobulin/Bikunin Precursor (Ambp), Collagen, type I, alpha 1 (Col1a1), Collagen, type I, alpha 2 (Col1a2), Collagen, type II, alpha 1 (Col2a1), Collagen, type III, alpha 1 (Col3a1), Hyaluronan synthase 1 (Has1), Hyaluronan synthase 2 (Has2), Hyaluronan synthase 3 (Has3), Inter-Alpha-Trypsin Inhibitor Heavy Chain 1 (Itih1) Inter-Alpha-Trypsin Inhibitor Heavy Chain 2 (ltih2), Stabilin 2 (Stab2), Tumor Necrosis Factor, Alpha-Induced Protein 6 (Tnfaip6) and Versican (Vcan).

10. The method of claim 1, wherein the therapy is surgical reconstruction.

11. The method of claim 1, wherein the therapy is viscosupplementation HA therapy.

* * * * *